United States Patent [19]

Amdur et al.

[11] Patent Number: 4,704,164

[45] Date of Patent: Nov. 3, 1987

[54] ORGANIC LIQUID BINDER COMPOSITION FOR PORCELAIN POWDERS

[75] Inventors: Benjamin H. Amdur, Westwood; Edwin J. Riley, Milton; Ralph B. Sozio, Boston, all of Mass.

[73] Assignee: Forsyth Dental Infirmary for Children, Boston, Mass.

[21] Appl. No.: 932,786

[22] Filed: Nov. 19, 1986

Related U.S. Application Data

[63] Continuation-in-part of Ser. No. 731,925, May 8, 1985, Pat. No. 4,645,454.

[51] Int. Cl.$^4$ ........................ A61C 13/00; C09K 3/00
[52] U.S. Cl. ................................. 106/35; 433/199.1; 433/201.1; 433/202.1; 433/212.1; 433/222.1

[58] Field of Search .................... 106/35, 308 Q, 311; 433/199.1, 201.1, 212.1, 222.1, 228, 203.1; 501/141; 252/182, 351, 352, 356, 363.5, 364

[56] References Cited

U.S. PATENT DOCUMENTS

| | | | |
|---|---|---|---|
| 3,880,662 | 4/1975 | Daskalon et al. | 106/35 |
| 4,557,691 | 12/1985 | Martin et al. | 106/35 |
| 4,604,059 | 8/1986 | Klaus et al. | 433/199.1 |
| 4,645,454 | 2/1987 | Amdur et al. | 433/199.1 |

Primary Examiner—Josephine L. Barr
Attorney, Agent, or Firm—Richard P. Crowley

[57] ABSTRACT

An organic liquid composition for use with a heat sinterable porcelain powder, such as dental porcelain powder, which binder composition comprises a mixture of organic liquids which have an index of refraction of the porcelain powder to be mixed with the organic liquid binder.

12 Claims, No Drawings

ORGANIC LIQUID BINDER COMPOSITION FOR PORCELAIN POWDERS

REFERENCE TO PRIOR APPLICATION

This application is a continuation in part of U.S. patent application Ser. No. 731,925, filed May 8, 1985, now U.S. Pat. No. 4,645,454, issued Feb. 24, 1987 which application is hereby incorporated by reference in its entirety. This application is directed to the non-elected claims of the parent application and contains additional examples of the organic liquid binder composition for use with procelain powder, particularly dental porcelain powder, to prepare heat sintered porcelain products.

BACKGROUND OF THE INVENTION

Ceramic powders have been utilized in dentistry for artificial teeth since the eighteenth century (Alexis Duchateau and Dubois de Chemat) and for fixed restorations (crowns) since the late nineteenth century (Dr. Charles H. Land). Porcelain powder for use by dentists and dental technicians for the building-up and shaping of dental appliances such as crowns, bridges, and artificial teeth is well known (see for example U.S. Pat. No. 3,400,097). Recent advances in technology have led to widespread use of procelains fused to various metals and other substructures such as crystalline ceramics. The various techniques involved in the use of porcelains for dental restorations all make use of a liquid binder to hold porcelain particles together to allow the powder to be built and shaped to the desired tooth form. After condensing and shaping, the liquid binder is removed from the mass, usually by heat, and the porcelain mass sintered.

The most common liquid binder used in dentistry is distilled water. Some manufacturers have tried additions of glycerine, propylene glycol or alcohol. Most additives are used to slow the drying process thus increasing the working time of the mix. Daskalon et al (U.S. Pat. No. 3,880,662, issued Apr. 29, 1975 hereby incorporated by reference) addressed this problem by substitution of part or all of the distilled water with water miscible polyhydric alcohols and ethers of alcohols. The usual procedure of shaping dental porcelain, however, remained to mix the dry powder with distilled water to a thick and creamy consistency and then apply it to the substructure (usually metal) with either a brush or spatula. The water is then withdrawn by wicking which causes the powder particles to pack more closely. This condensation of particles allows the mass to be shaped by carving. Keeping the mass moist during buildup is critical, since the powder can dry out rapidly and further placement of porcelain on a dry surface does not allow the understructure to be condensed properly. Restorations baked in such a way are more subject to air entrapment and can appear blotchy and opaque.

Proper application of porcelain powders is critical in constructing dental appliances and requires great skill not only for proper condensation, but also for correct development of color. The ceramist is required to place various shaded powders in order to achieve desired gradations of color and translucency in the finished product. This must be accomplished without seeing the true shades and modifications until the porcelain mix is sintered or vitrified. This requires great skill and imagination. Some dental porcelain manufacturers have tried to facilitate this process by the addition of organic dyes to allow differentiation of the blends of the various powders during the buildup. However, these colorants are arbitrary and bear no relation to the sintered shades.

SUMMARY OF THE INVENTION

The invention relates to liquid binders for use with porcelain powders to prepare heat sinterable porcelain mixes, to the porcelain mixes so prepared and to the method of preparing and fabricating sintered objects of desired color. In particular the invention concerns an organic liquid binder for use with dental porcelain powders and to the dental mixes prepared thereby, which liquid binder permits visualization of the true post-sintered color of the dental porcelain powder mix during application and prior to heat sintering to fabricate the dental appliance.

The invention relates to the use of organic liquid binders with porcelain powders and particularly dental porcelain powders to prepare sinterable porcelain mixes and which liquid binder allows visualization of the true post-sintered colors of the porcelain powders during application of the sinterable mix and prior to heat sintering of the mix. The organic non-aqueous liquid binder of the invention does not dry out under normal working conditions and posesses adhesive and cohesive properties conductive to the proper buildup when employed as an organic binder with porcelain powder. The liquid binder should have proper surface tension to permit wetting of the substructure in the fabrication of dental appliances and forms a gel-like mix with the porcelain powders minimizing hydraulic classification of the powder particles during condensation. The organic liquid binder also permits the dental porcelain powder mix to be supplied or stored in single packages or containers in a premixed state ready for use by the dentist or dental technician or ceramist and with actual color visualization of the post-sintered porcelain. At present dental porcelain powders and the distilled water or glycerine-water for mixing are supplied in separate containers and must be mixed immediately prior to use.

The present invention simplifies the buildup procedure in the construction of dental appliances and other ceramic products in two major ways. In the first way a liquid binder is used with slower volatilization so that the wet powder mix does not dry out during the buildup process. The mix can remain moist and workable until force dried. This decreases the skill required and allows interruption of work with no detrimental affects. In the second way by adjustment of the index of refraction of the liquid binder to match the index of refraction of the porcelain powder the true colors and shading of the mix can be visualized at the time of buildup and not only at or after the sintered stage. This represents a tremendous advantage to the ceramist as the color and shading modifications can be seen prior to sintering. This advance permits the artistic abilities of the ceramist, such as in the fields of art, industry, and dentistry to be better realized while requiring less skill in the fabrication of sintered porcelain products.

The liquid binders which constitute the present invention are single organic liquids or mixes of miscible organic liquids which have appropriate dispersivity and an index of refraction of the base glass frit used in porcelain powder such as a dental porcelain powder. These properties minimize light scattering by the particles of base glass and thus permit visualization of the true post-sintered color inherent in the porcelain powder composition during application and before firing or sintering. The organic liquid should also have the proper surface tension to allow wetting of the substructure and a suitable boiling point to allow evaporation of all the liquid prior to attainment of porcelain sintering temperatures. In addition, the liquid and its vapors should leave no residues that might react at firing temperatures and thus alter the properties of the base glass. The boiling point, index of refraction, dispersivity and rheologic properties are controlled by proper combination of the organic components in the liquid binder. A proper liquid binder also exhibits adhesive properties to the substrate and cohesive properties facilitating handling and buildup. Also by forming a gel-like mix with the porcelain powder, the organic liquid binder prevents hydraulic classification of the powder particles during condensation which can be a problem with existing aqueous compositions used with dental porcelain powders.

Various organic liquids may be used as the organic liquid binder in the invention either alone or in various combinations and typically such organic liquids so employed have a boiling point of over about 100° C. such as from about 110° to 144° C./85 mm Hg. Generally, the liquid binder has a refractive index which varies from about 1.4 to 1.6 and more typically around 1.49 to 1.56, such as 1.49 to 1.51. Thus, an individual organic liquid for use with present commercial dental powders may be employed where the liquid provides for the right index of refraction to match that of the porcelain powder to be employed or more commonly a combination of organic liquids is employed.

A wide variety of organic liquids may be used in various miscible proportions, such as for example, but not to be limited to: aryl-substituted alcohols such as the benzyl-substituted branched chain alcohol such as benzyl-substituted alkanols and more particularly the benzyl-tertiary-butanol or other similar carbinol-type liquids; alicyclic alcohols, and more particularly $C_7$–$C_6$ alicyclic alcohols such as cycloheptanol and cyclohexanol; aryl alcohols; alkyl esters of aryl acids; aryl estes of alkyl acids; alkyl-substituted alicylic ketones; alicyclic ketones; aryl-alkyl ethers; diaryl ethers; terpenoid alcohols; tertiary aliphatic alcohols; and branched chain aliphatic keto alcohols.

The organic liquid binder useful particularly with dental porcelain powder whether as a single organic liquid binder or an organic liquid binder composed of two, three, four or more liquids generally requires at least one liquid to have an aryl, e.g. a benzyl or phenyl group or an alicyclic group in order to obtain the necessary index of refraction. The liquid binder may comprise a single liquid such as an aryl alkyl ether like benzyl ethyl ether. Liquid binders which contain two or more liquids often include an aryl-containing alcohol such as a benzyl-substituted alaknol like benzyl-tertiary-butanol or benzyl alcohol. Other components may include, alone or in combination with the aryl-containing alcohols, alicyclic alcohols, aryl acetates, acyl alicyclic alcohols, benzyl ethyl ether, terpenoid alcohols, pentanones, etc. Some specific organic liquids useful, alone or in combination, include, but are not limited to: benzyl acetate; benzyl-tertiary-butanol; ethyl benzoate; phenyl acetate; 2-acetylcyclohexanone; cycloheptanol; cyclohexanol; benzyl alcohol; 4-hydroxy, 4-methyl, 2-pentanone; benzyl ethyl ether; nerol; phenethyl alcohol; cyclohexanone and combinations thereof.

Although various combinations of organic liquids may be used, a preferred organic binder is composed of a mixture of a benzyl-tertiary butanol (also known as phenylethyl dimethyl carbinol) and cycloheptanol which forms an organic solution having an index of refraction of 1.5068 at 25° C. and is suitable for use with most commercially available dental porcelain powders when employed in a ratio of 20 parts by volume of the benzyl-tertiary-butanol and one part by volume of the cycloheptanol. Another preferred organic liquid binder comprises 19 parts by volume of benzyl-tertiary-butanol, 1 part by volume cycloheptanol, and 20 parts by volume of benzylethyl ether with an index of refraction of $n_D^{25°\,C.}$ of 1.5002. These ratios provide: a proper surface tension and thus wetting of the substructure in the fabrication of a dental appliance; optimum rheological properties for forming; and optimum optical properties for the true color and shading visualization of the sinterable porcelain powder mix prior to sintering of the mix. If desired, various diluents to modify the handling properties of the mix may be used such as hydrocarbon esters, ketones, acids, ethers, and the like in varyng amounts. In addition, various soluble additives may be incorporated in the organic liquid binder if desired including stabilizers, antioxidants, diluents, surfactants, dispersing agents, and other additives in minor amounts as desired provided such additives do not interfere with the function of the organic binder or prevent the true color visualization prior to sintering.

In particular, it has been found that the organic liquid binder may comprise a solution of a benzyl-substituted alkanol, such as teritary butanol; an alicyclic alcohol such as cycloheptanol; and an alkylester of a dicarboxylic acid, such as a $C_2$ to $C_4$ alkyl di-ester of succinic acid, and particularly the di-ethyl ester of succinic acid. The solution may include, in addition, benzyl ether. The solution components may be used in varying amounts to receive the desired index of refraction, e.g. about 1.45 to 1.52. The amount of the various components may vary, for example, as follows: the benzyl alkanol, 35% to 95% by volume; the alicyclic alcohol, 1% to 8% by volume; the acid ester, 1% to 70% by volume; and the benzyl ether, 1% to 20% by volume.

The ratio of the organic liquids used in the liquid binder may vary so that the resulting liquid binder has the desired index of refraction. For example, where a benzyl-substituted alkanol is employed as one component and a alicyclic alcohol as another component the alkanol is typically employed in an amount from 80 to 99 percent by volume and more typically 90 to 98 percent by volume.

The liquid binders of the invention are usefully employed with a wide variety of porcelain powders to include and not be limited to dental porcelain powders employed for the purposes of fabricating dental appliances such as crowns, fixed bridges, artificial teeth and the like on a substructure or alone and as well as porcelain or particulate-type powders employed in other fields such as the fabrication of china, industrial ceramics, tile or other materials formed from porcelain powders or refractories where it is desired to provide a accurate color or shading in the resulting product. This would include metallo-porcelain art constructs.

Typically porcelain powders are comprises of one, or more commonly, a plurality of sinterable or vitrifiable metal oxides such as oxides of aluminum, magnesium, silicon, boron, or alkali metal or alkali earth metal such as sodium, potassium, calcium and the like, as well as silicates and phosphates. Such porcelain powder mixtures may also include other ingredients such as pigments, clays, binders, metal salts such as oxides for tint and color, and dyes. A typical dental porcelain powder may comprise a combination of aluminum oxide, silicon oxide, boron oxide, as well as potassium and sodium oxide. These powder mixtures are reacted at elevated temperatures to form a vitreous material which is ground to form a dental porcelain powder.

The amount of the liquid binder to be employed with the porcelain powders may vary as desired to provide the desired paste or gel-like consistency to form the object to be sintered, but usually, the organic liquid is used in amounts from about 10 to 50 percent by weight and more typically about 18 to 35 percent by weight of the total organic liquid and porcelain powder mix. The sinterable porcelain mix is prepared by admixing at room temperature the porcelain powder with the organic liquid.

The invention will be described for the purposes of illustration only in connection with certain embodiments; however, it is recognized that various changes, modifications, and improvements to these illustrative embodiments may be made by those persons skilled in the art falling within the spirit and scope of the invention. The embodiments will be described in connection with the preparation of dental appliances; however, it is recognized that the invention will find use in industrial and/or "artistic" ceramics and other fields where true color visualization and shading is desirable prior to sintering.

DESCRIPTION OF THE EMBODIMENTS

Various commercially available dental porcelain powders were mixed with the organic liquid bindrs and the pre- and post-fired colors compared. All commercially available porcelain powders tested were found to work well with the organic liquid binders to achieve the desired result. If a commercial dental porcelain powder were encountered with an index of refraction so different from the norm that the described liquid did not provide true color visualization before firing, the index of the organic liquid is readily adjusted, such as by the addition of other liquids or a change in composition to accommodate the index of refraction of the porcelain powder. The commercially available dental porcelain powders fall into two groups, those with organic dyes to help differentiate the layers of porcelain during buildup and those with no organic dyes present. An example of the use of each type is given.

EXAMPLE 1

A commercial dental porcelain powder with no organic dye colorants such as Cerestore ™ veneer (Johnson and Johnson Dental Products Company) is thoroughly mixed with a liquid binder of benzyl-tertiary-butanol and cycloheptanol (volume ratio of 20 to 1) to a paste or thick gel-like consistency which is easily lifted with a brush or small spatula. A ratio of approximately 1 gram of porcelain powder to 0.3 ml of the liquid binder gives the desired mix. The organic liquid binder had an index of refraction of $n_D^{25°\ C.}$ of 1.5068 which is the same or substantially the same as the porcelain powder used in the mix. The mix is then applied to the alumina substrate of the Cerestore ™ system in small increments. The mass is then alternately blotted with an absorbent tissue and vibrated to condense the powder mass as is done with the conventional techniques employing aqueous binders. Slumping during the procedure is considerably less than by comparison with a conventional porcelain-water mix and the technician has extended working time. With the liquid binder the porcelain powder can be premixed with the organic liquid binder and stored in containers ready for subsequent use.

The porcelain paste demonstrates the same shade prior to forced dryout and firing as in the post-fired crown.

After application of the various shaded porcelains the restoration is then dried, as in the conventional approach, by placing it in front of the open door of a furnace muffle for five to ten minutes depending on the size of the appliance. The retoration should completely dry out and turn chalky white before firing. It is then fired according to the particular manufacturer's recommendation to achieve vitrification. After removal from the furnace and cooling, the restoration will demonstrate the same color as the predried, prefired buildup.

EXAMPLE 2

In the case of commercial dental procelain powder such as Vita VMK 68 (Vident) which contains organic dyes for distinguishing blends of powders, the organic dyes must first be eliminated. The resultant white powders are then mixed with the organic liquid binder and utilized as in Example 1. The actual metal oxide colorants incorporated by the manufacturer are visualized at the buildup stage when the gel-like mix is applied to the metal substrate in the case of cermao-metal restorations or to platinum foil in the case of jacket crown restorations. This feature makes it easier for the technician to blend body and incisal portions of a tooth which is presently difficult and often done in two separate bakes. The liquid binder's capability of disclosing actual color of the fired porcelain before sintering also facilitates any necessary secondary firings, because further additions to the fired crown will have the appearance of the fired portion allowing the technician to realize the final effect on the shade of any modifications prior to additional bakes.

EXAMPLE 3

Example 1 was repeated employing as the organic liquid binder the following:
(a) Benzyl Acetate (1 vol)+and Benzyl-tert-butanol (1 vol)
 $n_D^{25°}=1.5027$
(b) Ethyl Benzoate 1 vol+Benzyl-tert-butanol 1 vol
 $n_D^{25°}=1.5047$
(c) Phenyl Acetate 1 vol+Benzyl-tert-butanol 1 vol
 $n_D^{25°}=1.5021$
(d) 2-Acetylcyclohexanone 4 vol+cycloheptanol 1 vol
 $n_D^{25°}=1.4865$
(e) Cyclohexanol 3.12 vol+Benzyl Alcohol 1.88 vol
 $n_D^{25°}=1.4905$
(f) 4-hydroxy, 4-methyl, 2-pentanone 1.94 vol+Benzyl Alcohol 3.06 vol
 $n_D^{25°}=1.4938$
(g) Cycloheptanol 1.94 vol+Benzyl Alcohol 3.06 vol
 $n_D^{25°}=1.4911$
(h) Benzyl ethyl ether
 $n_D^{20°}=1.4955$
(i) Benzyl-tert-butanol 1.17 vol+nerol 0.83 vol
 $n_D^{24°}=1.4948$
(j) Nerol 1.24 vol+Benzyl Alcohol 0.76 vol $n_D^{23°} = 1.4986$ (k) Benzyl-tert-butanol 19 vol+Cycloheptanol 1 vol+Benzyl ethyl ether 20 vol
$n_D^{23°} = 1.5002$ (l) Phenethyl alcohol 1.15 vol+Cyclohexanone 0.85 vol
$n_D^{20°} = 1.5000$ (m) benzyl-tert-butanol (56.7% vol), cycloheptanol (2.8% vol) and succinic acid di-ethyl ester (40.5% vol)
$n_D^{20°} = 1.470$ (n) benzyl-tert-butanol (85.7% vol.), cycloheptanol (4.3% vol), succinic acid di-ethyl ester (3.8% vol) and benzyl ether (6.2% vol)
$n_D^{20°} = 1.506$ (o) benzyl-tert-butanol (45.4% vol), cycloheptanol (2.2% vol) and succinic acid di-ethyl ester (52.4% vol)
$n_D^{20°} = 1.460$

What is claimed is:

1. An organic liquid binder composition adapted for use with heat sinterable porcelain powder, which binder composition allows visualization of the true post-sintered color of the porcelain powder prior to sintering and which liquid binder composition has an index of refraction of about 1.40 to 1.60 and comprises in combination a solution of:
   (a) benzyl-tert-butanol,
   (b) cycloheptanol; and
   (c) an alkyl ester of succinic acid.

2. The composition of claim 1 wherein the ester of succinic acid comprises the di-ethyl ester.

3. The composition of claim 1 which has an index of refraction of about 1.49 to 1.56.

4. The composition of claim 2 which includes benzyl ether.

5. The composition of claim 2 wherein the benzyl-tert-butanol comprises about 56.7% by volume, the cycloheptanol comprises about 2.8% by volume, and the succinic acid di-ethyl ester comprises about 40.5% by volume, and the composition has an index of refraction of about 1.470.

6. The composition of claim 4 wherein the benzyl-tert-butanol comprises about 85.7% by volume, the cycloheptanol comprises about 4.3% by volume, the succinic acid di-ethyl ester comprises about 3.8% by volume and the benzyl ether about 6.2% by volume, and the composition has an index of refraction of about 1.506.

7. The composition of claim 2 wherein the benzyl-tert-butanol comprises about 45.4% by volume, the cycloheptanol comprises about 2.2% by volume, and the succinic acid di-ethyl ester comprises about 52.4% by volume, and the composition has an index of refraction of about 1.460.

8. The composition of claim 1 wherein the benzyl-tert-butanol ranges from about 35% to 95% by volume.

9. The composition of claim 1 wherein the cycloheptanol ranges from about 1% to 8% by volume.

10. The composition of claim 1 wherein the alkyl ester of succinic acid ranges from about 1% to 70% by volume.

11. The composition of claim 4 wherein the benzyl ether ranges from about 1% to 20% by volume.

12. The composition of claim 1 which includes a heat sinterable porcelain powder admixed with the binder composition.

* * * * *